(12) United States Patent
Ran et al.

(10) Patent No.: US 11,105,798 B2
(45) Date of Patent: Aug. 31, 2021

(54) DEVICE AND METHOD FOR CAPILLARY CHEMILUMINESCENCE DETECTION

(71) Applicants: CHENGDU POLYTECH BIOLOGICAL TECHNOLOGY CO., LTD, Chengdu (CN); CHENGDU SEAMATY TECHNOLOGY CO., LTD, Chengdu (CN)

(72) Inventors: Peng Ran, Chengdu (CN); Zihua Han, Chengdu (CN); Yunxuan Tang, Chengdu (CN); Peng Wang, Chengdu (CN)

(73) Assignees: CHENGDU POLYTECH BIOLOGICAL TECHNOLOGY CO., LTD, Chengdu (CN); CHENGDU SEAMATY TECHNOLOGY CO., LTD, Chengdu (CN)

( * ) Notice: Subject to any disclaimer, the term of this patent is extended or adjusted under 35 U.S.C. 154(b) by 313 days.

(21) Appl. No.: 16/319,027

(22) PCT Filed: Jul. 11, 2017

(86) PCT No.: PCT/CN2017/092446
§ 371 (c)(1),
(2) Date: Jan. 18, 2019

(87) PCT Pub. No.: WO2018/218738
PCT Pub. Date: Dec. 6, 2018

(65) Prior Publication Data
US 2019/0277837 A1    Sep. 12, 2019

(30) Foreign Application Priority Data
Jun. 2, 2017    (CN) .................. 201710408023.X

(51) Int. Cl.
*B01L 3/00*   (2006.01)
*G01N 33/53*  (2006.01)
(Continued)

(52) U.S. Cl.
CPC .......... *G01N 33/5302* (2013.01); *B01L 3/523* (2013.01); *B01L 3/527* (2013.01);
(Continued)

(58) Field of Classification Search
None
See application file for complete search history.

(56) References Cited

U.S. PATENT DOCUMENTS 4,980,293 A * 12/1990 Jeffs .................. B01L 3/508
422/561
5,462,881 A * 10/1995 Perlman ............. B01L 3/502
422/548

FOREIGN PATENT DOCUMENTS

CN    203849047    9/2014
CN    105214744    1/2016

OTHER PUBLICATIONS

Shen et al., "Immunoassay for Alpha Fetal Protein in Serum Based on Quartz Capillary Materials by Gray Level Analysis", Chinese Journal of Analytical Chemistry, vol. 45, Jan. 2017, pp. 83-88.
(Continued)

*Primary Examiner* — Rebecca M Giere
(74) *Attorney, Agent, or Firm* — Hauptman Ham, LLP

(57) ABSTRACT

The present invention discloses a device and a method for capillary chemiluminescence detection. The device comprises a liquid adding device, wherein the liquid adding device comprises: a bottom end of a funnel cup connected to a top end of the capillary body; a mounting bracket with one or more grooves; a liquid reagent cup disposed in each of the one or more grooves, a reagent set in the cup body, and a
(Continued)

sealing film disposed at the opening of the cup body, a bottom end of each of the one or more grooves is connected to a top end of the funnel cup; a puncture device disposed in an inner bottom end of each of the one or more grooves. The present invention has the advantages of reducing the cost of the instrument, improving the reliability of the operation and so on.

10 Claims, 2 Drawing Sheets

(51) Int. Cl.
*B01L 9/00* (2006.01)
*G01N 33/543* (2006.01)
*G01N 21/76* (2006.01)

(52) U.S. Cl.
CPC .......... *B01L 9/00* (2013.01); *G01N 33/54366* (2013.01); *B01L 2300/044* (2013.01); *B01L 2300/08* (2013.01); *B01L 2300/12* (2013.01); *B01L 2300/123* (2013.01); *B01L 2400/0406* (2013.01); *G01N 21/76* (2013.01)

(56) References Cited

OTHER PUBLICATIONS

International search report dated Feb. 28, 2018 from corresponding application No. PCT/CN2017/092446.

\* cited by examiner

DEVICE AND METHOD FOR CAPILLARY CHEMILUMINESCENCE DETECTION

RELATED APPLICATIONS

The present application is a National Phase of International Application Number PCT/CN2017/092446, filed Jul. 11, 2017, and claims the priority of China Application No. 201710408023.X, filed Jun. 2, 2017.

FIELD OF THE INVENTION

The present invention relates to the field of chemiluminescence detection, and more particularly to a device and a method for capillary chemiluminescence detection.

BACKGROUND OF THE INVENTION

The disposable point sample capillary has a capillary phenomenon of automatic liquid absorption, which can achieve automatic adding, but only be effective when used for the first time. The same capillary which had been used once again using the capillary phenomenon to add the liquid will cause the contamination of the liquid source used later. So when the capillary is used as a disposable reaction container, a multi-step way reaction like an immune experiment is unable to carry on; during the immune experiment, two kinds of antibodies or antigens are used to combine the under test antigen or antibody, and the general reagents such as a washing fluid and a substrates are also used for assisting the experiment. If the capillary is used as a fixed reaction vessel, an additional cleaning device and cleaning process are required.

Some products of the micro-flow control chip, which has sprung up in recent years, also use capillary as a reaction container for immune reaction. Such as in CN201510696773.2, the products which use the capillary as a micro-flow control reaction container or channel will integrate all the liquid reagents into the chip, to achieve a single-individual packaging; but these products only use the characteristic of small size of the capillary, to minimize the amount of the reagent, and the capillary is only used as a reaction channel or container. In order to achieve an accurate quantitative reaction, all the reagents are integrated into the chip; the adopted power system and liquid adding system which must be able to achieve a very high precision are very complex, so the price of instruments and consumables of such micro-flow control chips will be high, and the working stability of the overall system will also be greatly reduced.

BRIEF SUMMARY OF THE INVENTION

The technical problems to be solved by the present invention are as follows: in prior art, the capillary used as a disposable reaction vessel is unable to be used for a multi-step way reaction like an immune experiment, while using capillary as a immune reaction container has the problems of high cost, insufficient working stability and pollution of liquid source. The aim of the present invention is to provide a device and a method for capillary chemiluminescence detection, which can not only effectively use capillary as a disposable reaction container, reduce the amount of reagent, and effectively solve the problem of reagent source pollution, but also use the small size of capillary itself to achieve the control of the reaction volume, reduce the need for sampling accuracy. The present invention not only reduces the cost of the instrument, but also improves the reliability of the operation.

The technical scheme of the present invention is as follows:

A device for capillary chemiluminescence detection, comprising a liquid adding device for adding reagents to a capillary body, wherein the liquid adding device comprises: a bottom end of a funnel cup connected to a top end of the capillary body; a mounting bracket with one or more grooves; a liquid reagent cup disposed in each of the one or more grooves for holding reagent, wherein the liquid reagent cup consists of a cup body with an opening, a reagent set in the cup body, and a sealing film disposed at the opening of the cup body, a bottom end of each of the one or more grooves is connected to a top end of the funnel cup; a puncture device disposed in an inner bottom end of each of the one or more grooves for piercing the sealing film to allow the reagent in the liquid reagent cup to flow into the funnel cup when the liquid reagent cup is pressed under pressure.

The opening of the liquid reagent cup of the present invention is downward into the liquid adding device, and the puncture device designed to pierce the sealing film is disposed on the corresponding liquid adding device under the liquid reagent cup. When a liquid reagent needs to be added, liquid reagent cup is pressed by a manual or a moving mechanism of the supporting instrument, the sealing film on the liquid reagent cup is pierced by the puncture device, continued to be squeezed, and the liquid flows out. Because the position of the puncture device is higher than that of the opening at the upper end of the capillary body, the liquid flows to the upper end of the capillary body under the action of gravity, and then flows into the interior of the capillary body under the joint action of the capillarity of the capillary body and the gravity of the liquid itself. When the gravity of the liquid is greater than the capillary force, the liquid flows out of the opening at the lower end of the capillary body and decreases; and the liquid stops flowing out and maintains a stable state within the capillary until its gravity is equal to the capillary force. When the liquid reagent reaction or the cleaning ends, the manual or the capillary liquid releasing mechanism of the supporting instrument is used to press, a high pressure gas is blown out to blow out the liquid in the capillary body from the opening at the lower end of the capillary body, and the liquid falls into the bottom waste liquid collector; the blowing process lasts 2 s-10 s, which can effectively ensure that all liquids are blown out.

Meanwhile, the capillary has the capillary phenomenon, which is a phenomenon that occurs in the capillary which is small enough to be comparable to the curvature radius of a liquid curved moon surface. The entire liquid surface in the capillary will be curved, the interaction between the liquid-solid molecules can be extended to the entire liquid, then the liquid surface is similar to a tight rubber film. If the liquid surface is curved, it has a tendency to flatten. Therefore, the concave liquid surface exerts a pulling force on the liquid below, the convex liquid surface exerts a pressure on the liquid below. If the liquid surface of the infiltrating liquid in the capillary is concave, the liquid surface exerts a pulling force on the liquid below, allowing the liquid to rise along the wall of the tube. When the upward pull is equal to the gravity of the liquid column in the tube, the liquid in the tube stops rising and reaches equilibrium.

Therefore, the present invention integrates the capillary body used as the disposable reaction container with the liquid adding device having a variety of liquid reagent cups together, and the liquid reagent is independently encapsulated into the liquid reagent cup according to the single reaction demand quantity. The purpose of chemical luminescence reaction on a single capillary can be achieved by simply squeezing the liquid reagent cup in turn according to the subsequent experimental process, and releasing the liquid into the capillary body to react. The above method can not only solve the problem of the contamination of the reagent source when a variety of reagents are added into the disposable capillary, but also omit the measure operation of the immune reaction reagent in the immune reaction, reduce the labor intensity of the measure of the immune reaction reagent, avoid the human error in the process of measuring, and improve the stability of the detection.

At the same time, the present invention also uses the small size of the capillary itself to realize the control of the reaction volume, not only to achieve the effect of reducing the amount of reagent during detection by use of the capillary structure in prior art, but also, through the combination of the optimization of the present invention structure and the principle of capillary phenomenon, to effectively reduce the need for sampling accuracy. Thus, compared with the prior art, the present invention not only reduces the cost of the instrument, but also improves the reliability of the operation.

Furthermore, an inner of the capillary body is coated with an antibody or an antigen; the amount of the one or more grooves disposed on the mounting bracket is three or more; each of a plurality of the liquid reagent cups comprises a reagent; the reagents in the liquid adding device comprise three types of a washing fluid, a reagent for catching the antibody or the antigen, and a substrate.

Preferably, the amount of the one or more grooves disposed on the mounting bracket is four, the reagents in the liquid reagent cups in two of the one or more grooves comprise the washing fluid, the reagent in the liquid reagent cup in another of the one or more grooves comprises the reagent for catching the antibody or the antigen, and the reagent in the liquid reagent cup in the last of the one or more grooves comprises the substrate.

Furthermore, the capillary body is made of a glass, a quartz or a polystyrene material, the tube length of the capillary body is 20~100 mm, the inner diameter of the capillary body is 0.2~1 mm, and the sealing film is made of an aluminum-plastic film or a polytetrafluoroethylene film.

In order to better flow the liquid in the liquid reagent cup into the capillary body, a convex piece is disposed on the bottom end of each of the one or more grooves, and the puncture device is fixed on a top end of the convex piece; assuming that L represents the height of the one or more grooves, a represents the height of the convex piece, b represents the height of the puncture device, and c represents the height of the liquid reagent cup, that is: $L \geq a+b+c$. Through the setting of the above structure, the batch inflow of the reagent in liquid reagent cup into the capillary body also can be effectively realized.

Moreover, through the above setting, not only the pressure operation of the liquid reagent cup can be effectively facilitated, so that the reagent in the liquid reagent cup can better flow into the capillary body, but also the upper surface of the liquid reagent cup being higher than that of the one or more grooves can be effectively avoided, and thus the situation of the sealing film on the liquid reagent cup damaged by the puncture device caused by the external force accidentally can be reduced.

Furthermore, the shape of the liquid reagent cup matches the shape of each of the one or more grooves. Through the optimal setting of the structure, the reagent in the liquid reagent cup can be fully pressed out during the pressing process of the liquid reagent cup, so as to better ensure that the reagent can flow into the capillary body and improve the detection stability.

A method for capillary chemiluminescence detection, comprising the following steps:

(1) adding the sample solution to the capillary body;

(2) the antibody or antigen in the sample solution reacts with the antibody or antigen in the capillary body, after the reaction is completed, blowing at the top end of the capillary body to discharge the liquid from the capillary body;

(3) pressing down the liquid reagent cup containing washing fluid to flush the capillary body, and after the cleaning is completed, blowing out the liquid in the capillary body by a capillary liquid release mechanism;

(4) pressing down the liquid reagent cup containing the reagent for catching the antibody or the antigen to make the reagent for catching the antibody or the antigen flow into the capillary body to react, and after the reaction is completed, blowing out the liquid in the capillary body;

(5) repeating step (3) to clean the capillary body;

(6) pressing down the liquid reagent cup containing the substrate to make the substrate release and flow into the capillary body, and after the reaction of the substrate and the material in the capillary body is completed, the test can be carried on.

Furthermore, the washing fluid flushing the capillary body in step (3) comprises the following steps: pressing down one third of strokes of the liquid reagent cup containing washing fluid to squeeze the sealing film, and when the washing fluid flushes into the capillary body and reaches a stable state, blowing out all of the liquid in the capillary body; then pressing down another one third of the strokes, and when the washing fluid flushes into the capillary body and reaches a stable state, blowing out all of the liquid in the capillary body; and then pressing down all of the strokes of the liquid reagent cup to press out all of the liquid, when the washing fluid flushes into the capillary body and reaches a stable state, blowing out all of the liquid in the capillary body.

The optimization of the above step (3) can effectively ensure that the residual inside the capillary body is rinsed clean, and improve the detection accuracy.

Compared with the prior art, the present invention has advantages and beneficial effects as follows:

1. The present invention can perform a chemiluminescence reaction on a single capillary, reduce the amount of the reagent in the immune reaction, avoid the contamination of the reagent source, realize the independently package of the single reagent, simplify the measure work of the immune reaction reagent in the immune reaction, maximum reduce the human error of the measure, reduce the workload, and improve the stability of the detection.

2. The present invention uses the small size of the capillary itself and the principle of capillarity to realize the control of the reaction volume, reduce the need for sampling accuracy. The present invention not only reduces the cost of the instrument, but also improves the reliability of the operation.

BRIEF DESCRIPTION OF THE DRAWINGS

The present invention will become more readily apparent to those ordinarily skilled in the art after reviewing the following detailed description and accompanying drawing, in which: the drawings described herein are used to provide a further understanding for the embodiment of the present invention and form part of this application and do not constitute a qualification for the embodiment of the present invention. In the following drawings.

Annotations in the figures and names of the corresponding parts are.

Figure 1:
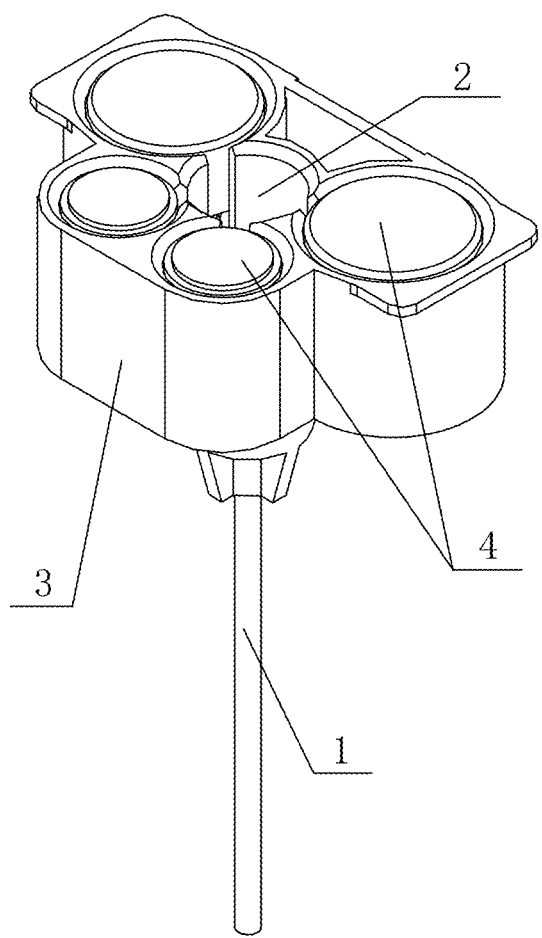
FIG. 1 is a schematic view of the present invention.

1-Capillary body, 2-Funnel cup, 3-Mounting bracket, 4-Liquid reagent cup, 5-Convex piece, 6-Puncture device; 41-Cup body, 42-Sealing film.

DETAILED DESCRIPTION OF THE PREFERRED EMBODIMENTS

In order to make the purpose, technical scheme and advantages of the present invention more clarity and understanding, a further detailed description of the present invention is provided in conjunction with embodiments and drawings. The schematic embodiment of the present invention and its description are only used to explain the present invention, but not served as a qualification for the present invention.

Embodiment 1

A device for capillary chemiluminescence detection, comprising the liquid adding device for adding reagents to the capillary body 1, wherein the capillary body 1 in this embodiment is made of the glass, the tube length of the capillary body 1 is 40 mm, the inner diameter of the capillary body 1 is 0.6 mm.

The liquid adding device comprises the funnel cup 2, the mounting bracket 3, the liquid reagent cup 4 and the puncture device 6, and the specific structures are as follows:

the funnel cup 2 connects to the top end of the capillary body 1, the mounting bracket is disposed on the top end of the funnel cup 2, one or more grooves are set on the mounting bracket 3, the bottom end of the one or more grooves are connected to the top end of the funnel cup 2, the puncture device is disposed on the bottom end of each of the one or more grooves, the liquid reagent cup 4 is set in each of the one or more grooves.

Meanwhile, the present invention also optimizes the structure of the liquid reagent cup 4 to promote the reagent in the liquid reagent cup 4 to flow into the capillary body 1 during the pressing down process of the liquid reagent cup 4, and the specific setting mode is as follows: the liquid reagent cup consists of a cup body 41 with an opening, a reagent set in the cup body, and a sealing film 42 disposed at the opening of the cup body; the opening of the liquid reagent cup 4 is downward, during the pressing process of the cup body 41, the puncture device 6 can pierce the sealing film 42, and then the liquid sealed in the liquid Reagent Cup 4 is released into each of the one or more grooves and then flows into the capillary body 1 through the funnel cup 2.

Figure 2:
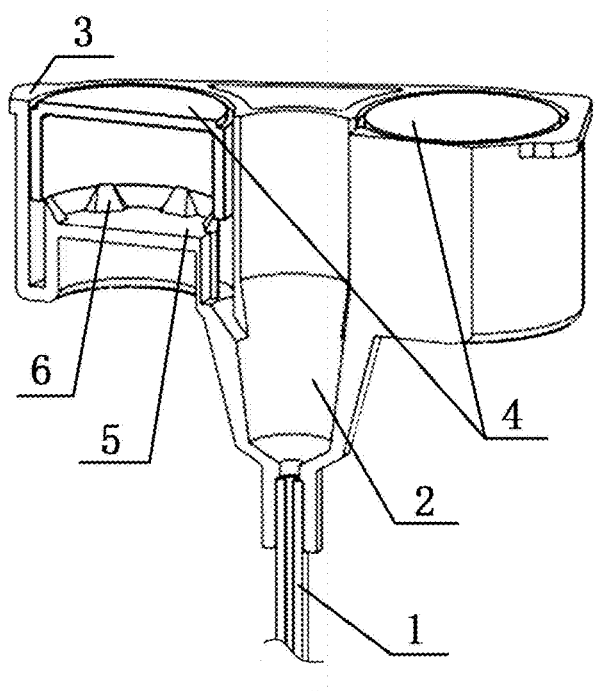
FIG. 2 is a schematic view of the inner structure of the present invention.
Figure 3:
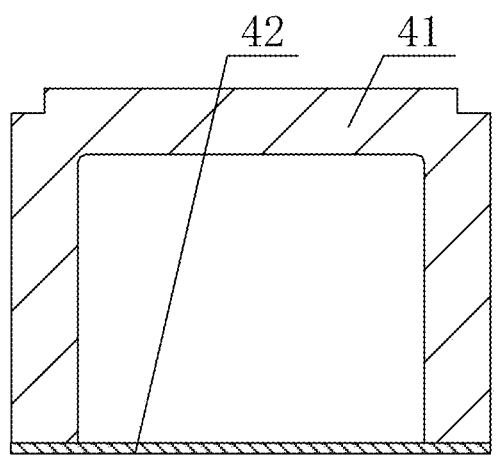
FIG. 3 is a schematic view of the section structure of the liquid reagent cup of the present invention.

As shown in FIG. 1 to FIG. 3, the amount of the one or more grooves disposed on the mounting bracket is preferably four in this embodiment; the reagents in the liquid reagent cups in two of the one or more grooves comprise the washing fluid, the reagent in the liquid reagent cup in another of the one or more grooves comprises the reagent for catching the antibody or the antigen, and the reagent in the liquid reagent cup in the last of the one or more grooves comprises the substrate The specific detection method of the above capillary chemiluminescence detection device is as follows:

(1) adding proper amount of the sample from the position of the funnel cup 2 shown in FIG. 1 by the manual pipette, and then putting the sample in the reaction area to react; or using the mechanical device to grab the liquid adding device with the capillary body 1 to the sample suction position, dropping a vacuum suction similar to the pipette to tightly integrate with the inner wall of the funnel cup 2; when the lower end of the capillary body 1 is immersed into the sample solution, activating the vacuum device disposed in the supporting instrument to extract negative pressure and inhale the sample solution into the capillary body 1; after the vacuum suction detached from the inner wall of the funnel cup 2, using the mechanical device to grab the liquid adding device to the reaction area to react;

in this embodiment, the mechanical device is used to absorb the sample solution;

(2) under the condition of 37 degrees constant temperature in the reaction area, the antibody or antigen in the sample solution reacts with the antibody or antigen in the capillary body for the first time; after the reaction is completed, blowing out the liquid in the capillary body by the manual, or moving down the automatic blowing mechanism of the supporting instrument to the top end of the funnel cup, and blowing at the top end of the capillary body by the automatic blowing mechanism to discharge the liquid in the capillary body;

(3) pressing down the liquid reagent cup containing washing fluid by the manual or the capillary liquid releasing mechanism of the supporting instrument to flush the capillary body, and after the cleaning is completed, blowing out the liquid in the capillary body by the manual or the automatic blowing mechanism of the supporting instrument;

(4) pressing down the liquid reagent cup containing the reagent for catching the antibody or the antigen by the manual or the capillary liquid releasing mechanism of the supporting instrument to make the reagent for catching the antibody or the antigen flow into the funnel cup along the ramp between the liquid reagent cup and the funnel cup; under the action of the gravity of the reagent itself and the capillarity of the capillary body, the reagent flows into the interior of the capillary body to make the reagent for catching the antibody or the antigen reaction with the material in the capillary body for the second time; after the reaction is completed, blowing out the liquid in the capillary body by the manual or the capillary liquid releasing mechanism of the supporting instrument;

(5) repeating the step (3) to clean the capillary body;

(6) pressing down the liquid reagent cup containing the substrate by the manual or the capillary liquid releasing mechanism to make the substrate release and flow into the capillary body, and after the reaction of the substrate and the material in the capillary body is completed, the reacted capillary can be tested for optical detection.

Embodiment 2

The difference between this embodiment and embodiment 1 is that, the materials of the capillary body and the sealing film are optimized in this embodiment; in this embodiment, the capillary body is made of the polystyrene material, and the sealing film is made of the aluminum-plastic film.

Embodiment 3

As shown in FIG. 2, the difference between this embodiment and embodiment 1 is that, the structure of the one or more grooves is optimized in this embodiment, the specific setting is as follows:

a convex piece 5 is disposed on the bottom end of each of the one or more grooves, and the puncture device 6 is fixed on a top end of the convex piece 5; assuming that L represents the height of the one or more grooves, a represents the height of the convex piece 5, b represents the height of the puncture device 6, and c represents the height of the liquid reagent cup 4, that is: L≥a+b+c; the shape of the liquid reagent cup matches the shape of each of the one or more grooves;

in this embodiment, the height value of the one or more grooves L is equal to that of the sum of the height of the convex piece 5, the height of the puncture device 6, and the height of the liquid reagent cup 4, that is, L=a+b+c.

Embodiment 4

The difference between this embodiment and embodiment 1 is that, the cleaning process in the steps (3) and steps (5) is different in this embodiment, the specific setting is as follows:

pressing down about one third of the highest of the liquid reagent cup containing washing fluid by the manual or the capillary liquid releasing mechanism of the supporting instrument to squeeze the sealing film, and when the washing fluid flushes into the capillary body and reaches the stable state, blowing out all of the liquid in the capillary body by the manual or the automatic blowing mechanism of the supporting instrument; and then pressing down another about one third of the highest of the liquid reagent cup, and when the washing fluid flushes into the capillary body and reaches the stable state again, blowing out all of the liquid in the capillary body by the manual or the automatic blowing mechanism of the supporting instrument; finally, pressing down all of the highest of the liquid reagent cup to press out all of the liquid, when the washing fluid flushes into the capillary body and reaches a stable state for the last time, blowing out all of the liquid in the capillary body by the manual or the automatic blowing mechanism of the supporting instrument. According to the setting of the method in this embodiment, the cleaning effect can be effectively increased.

While the purpose, technical scheme and beneficial effect of the present invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A device for capillary chemiluminescence testing, wherein, the device comprises:
    a liquid adding device for adding reagents to a capillary body, wherein the liquid adding device comprises:
        a bottom end of a funnel cup connected to a top end of the capillary body;
        a mounting bracket with one or more grooves;
        a liquid reagent cup disposed in each of the one or more grooves for holding a reagent, wherein the liquid reagent cup consists of a cup body with an opening, a reagent set in the cup body, and a sealing film disposed at the opening of the cup body, a bottom end of each of the one or more grooves is connected to a top end of the funnel cup; and
        a puncture device disposed in an inner bottom end of each of the one or more grooves for piercing the sealing film to allow the reagent in the liquid reagent cup to flow into the funnel cup when the liquid reagent cup is pressed under pressure.

2. The device for capillary chemiluminescence testing according to claim 1, wherein,
    an inner surface of the capillary body is coated with an antibody or an antigen; the amount of the one or more grooves disposed on the mounting bracket is three or more; and
    the liquid reagent cup in each of the three or more grooves comprises a reagent and a substrate; the reagent in the liquid adding device is selected from the group consisting of a washing fluid, a reagent for catching the antibody and the antigen.

3. The device for capillary chemiluminescence testing according to claim 2, wherein,
    a number of the three or more grooves disposed on the mounting bracket is four, the reagents in the liquid reagent cups in two of the four grooves comprise the washing fluid, the reagent in the liquid reagent cup in a third of the four grooves comprises the reagent for catching the antibody or the antigen, and the reagent in the liquid reagent cup in a fourth of the four grooves comprises the substrate.

4. The device for capillary chemiluminescence testing according to claim 1, wherein, the capillary body is made of a glass, a quartz or a polystyrene material.

5. The device for capillary chemiluminescence detection according to claim 1, wherein, the tube length of the capillary body is 20-100 mm and the inner diameter is 0.2-1 mm.

6. The device for capillary chemiluminescence testing according to claim 1, wherein, the sealing film is made of an aluminum-plastic film or a polytetrafluoroethylene film.

7. The device for capillary chemiluminescence testing according to claim 1, wherein, a convex piece is disposed on the bottom end of each of the one or more grooves, and the puncture device is fixed on a top end of the convex piece; assuming that L represents the height of the one or more grooves, a represents the height of the convex piece, b represents the height of the puncture device, and c represents the height of the liquid reagent cup, that is: L≥a+b+c.

8. The device for capillary chemiluminescence testing according to claim 1, wherein, the shape of the liquid reagent cup matches the shape of the one or more grooves.

9. A method for capillary chemiluminescence testing using the device of claim 1, wherein, the method comprises the following steps:
    (1) adding a sample solution to the capillary body;
    (2) after a reaction of an antibody or antigen in the sample solution and the antibody or antigen in the capillary body is completed, blowing at a top end of the capillary body to discharge a liquid from the capillary body;
    (3) pressing down the liquid reagent cup containing washing fluid to flush the capillary body, and after a cleaning is completed, blowing out the liquid in the capillary body by capillary liquid release mechanism;
    (4) pressing down the liquid reagent cup containing the reagent for catching the antibody or the antigen to make the reagent for catching the antibody or the antigen flow into the capillary body to react, and after the reaction is completed, blowing out the liquid in the capillary body;
    (5) repeating the step (3) to clean the capillary body;

(6) pressing down the liquid reagent cup containing a substrate to make the substrate release and flow into the capillary body, and after the reaction of the substrate and the material in the capillary body is completed, a test is conducted.

10. The method for capillary chemiluminescence testing according to claim 9, wherein, the washing fluid flushing the capillary body in step (3) comprises the following steps:

pressing down one third of strokes of the liquid reagent cup containing washing fluid to squeeze a sealing film, and when the washing fluid flushes into the capillary body and reaches a stable state, blowing out all of the liquid in the capillary body;

then pressing down another one third of the strokes, and when the washing fluid flushes into the capillary body and reaches a stable state, blowing out all of the liquid in the capillary body; and then pressing down all of the strokes of the liquid reagent cup to press out all of the liquid, when the washing fluid flushes into the capillary body and reaches a stable state, blowing out all of the liquid in the capillary body.

\* \* \* \* \*